United States Patent
Dyballa et al.

(10) Patent No.: US 9,617,290 B2
(45) Date of Patent: Apr. 11, 2017

(54) BISPHOSPHITES HAVING AN OUTER NAPHTHYL-PHENYL UNIT

(71) Applicants: Katrin Marie Dyballa, Recklinghausen (DE); Robert Franke, Marl (DE); Dirk Fridag, Haltern am See (DE); Armin Boerner, Rostock (DE); Detlef Selent, Rostock (DE)

(72) Inventors: Katrin Marie Dyballa, Recklinghausen (DE); Robert Franke, Marl (DE); Dirk Fridag, Haltern am See (DE); Armin Boerner, Rostock (DE); Detlef Selent, Rostock (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/955,176

(22) Filed: Dec. 1, 2015

(65) Prior Publication Data
US 2016/0159835 A1   Jun. 9, 2016

(30) Foreign Application Priority Data

Dec. 4, 2014   (EP) .................................... 14196189

(51) Int. Cl.
| C07F 9/6571 | (2006.01) |
| C07F 9/6574 | (2006.01) |
| C07C 45/50 | (2006.01) |

(52) U.S. Cl.
CPC ............ *C07F 9/6571* (2013.01); *C07C 45/50* (2013.01); *C07F 9/65746* (2013.01)

(58) Field of Classification Search
CPC ..... C07F 9/6571; C07F 9/65746; C07C 45/50
USPC ...................................................... 568/13, 17
See application file for complete search history.

(56) References Cited

U.S. PATENT DOCUMENTS

| 5,688,986 A | 11/1997 | Tam et al. |
| 5,723,641 A | 3/1998 | Tam et al. |
| 2015/0290633 A1 | 10/2015 | Christiansen et al. |

FOREIGN PATENT DOCUMENTS

| WO | WO 95/14659 A1 | 6/1995 |
| WO | WO 2014/056733 A1 | 4/2014 |

OTHER PUBLICATIONS

Search Report issued Apr. 29, 2015 in European Patent Application No. EP 14 19 6189 (with English translation of Categories of Cited Documents).

*Primary Examiner* — Porfirio Nazario Gonzalez
(74) *Attorney, Agent, or Firm* — Oblon, McClelland, Maier & Neustadt, L.L.P.

(57) ABSTRACT

Bisphosphites having an outer naphthyl-phenyl unit.

11 Claims, 1 Drawing Sheet

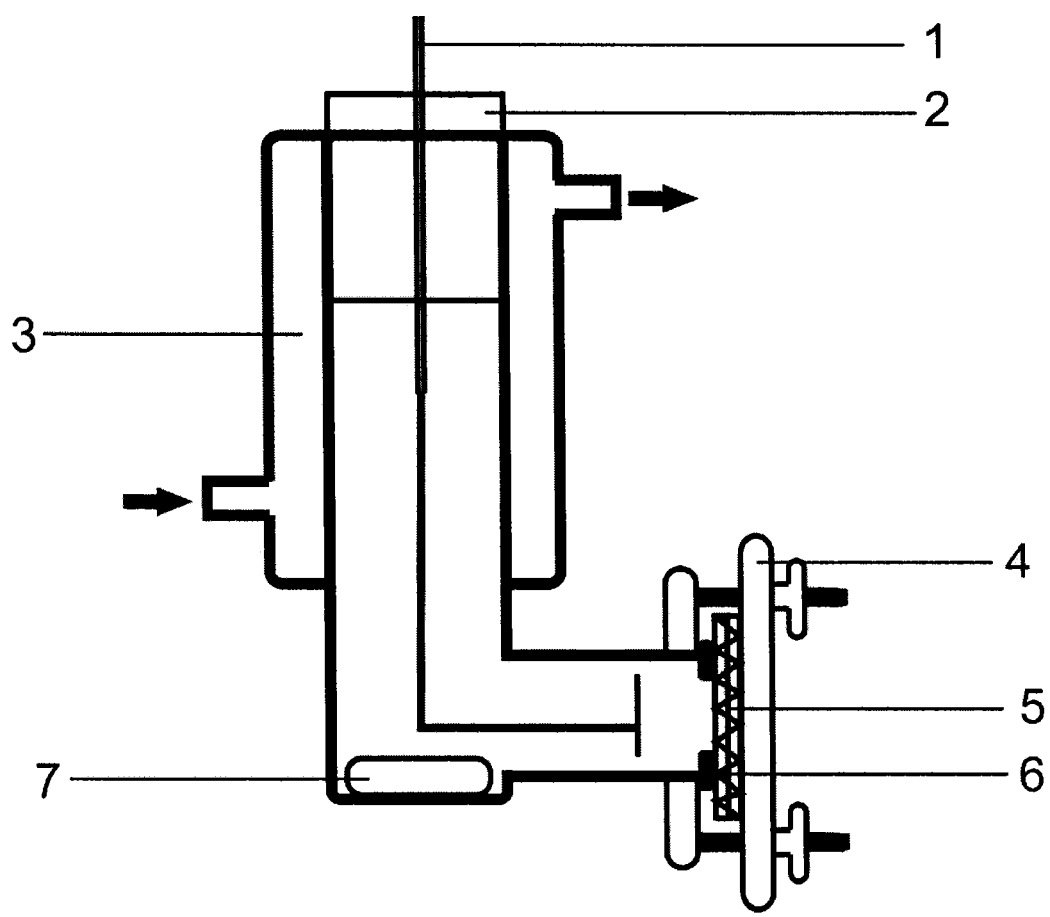

BISPHOSPHITES HAVING AN OUTER NAPHTHYL-PHENYL UNIT

The invention relates to bisphosphites having an outer naphthyl-phenyl unit.

A bisphosphite has a central unit, called the backbone, and two outer units bonded to the central unit via the phosphorus atom.

The bisphosphites according to the invention have at least one outer naphthyl-phenyl unit. It is also possible for the two outer units to have a naphthyl-phenyl unit. It is further possible for the central unit to additionally also have a naphthyl phenyl unit.

DE 10 2006 058 682 A1 discloses bisphosphites having different yet symmetrical outer units, for example compound 1b on page 8 of DE 10 2006 058 682 A1.

The problem addressed by the invention was that of providing bisphosphites having a novel structure compared to the bisphosphites known in the literature.

The object is achieved by a compound according to Claim 1.

Compound having one of the four general structures I to IV:

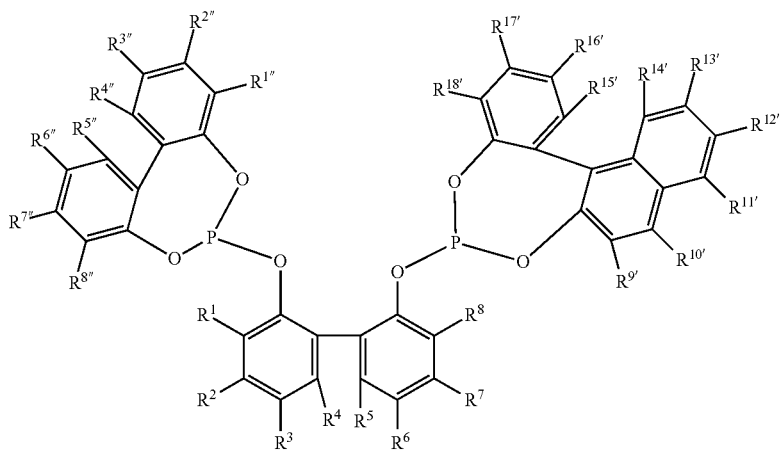

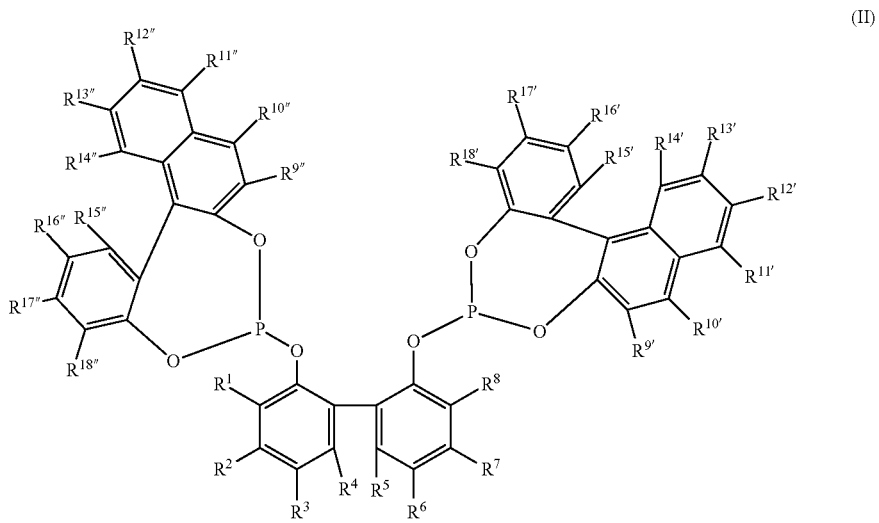

-continued (III)

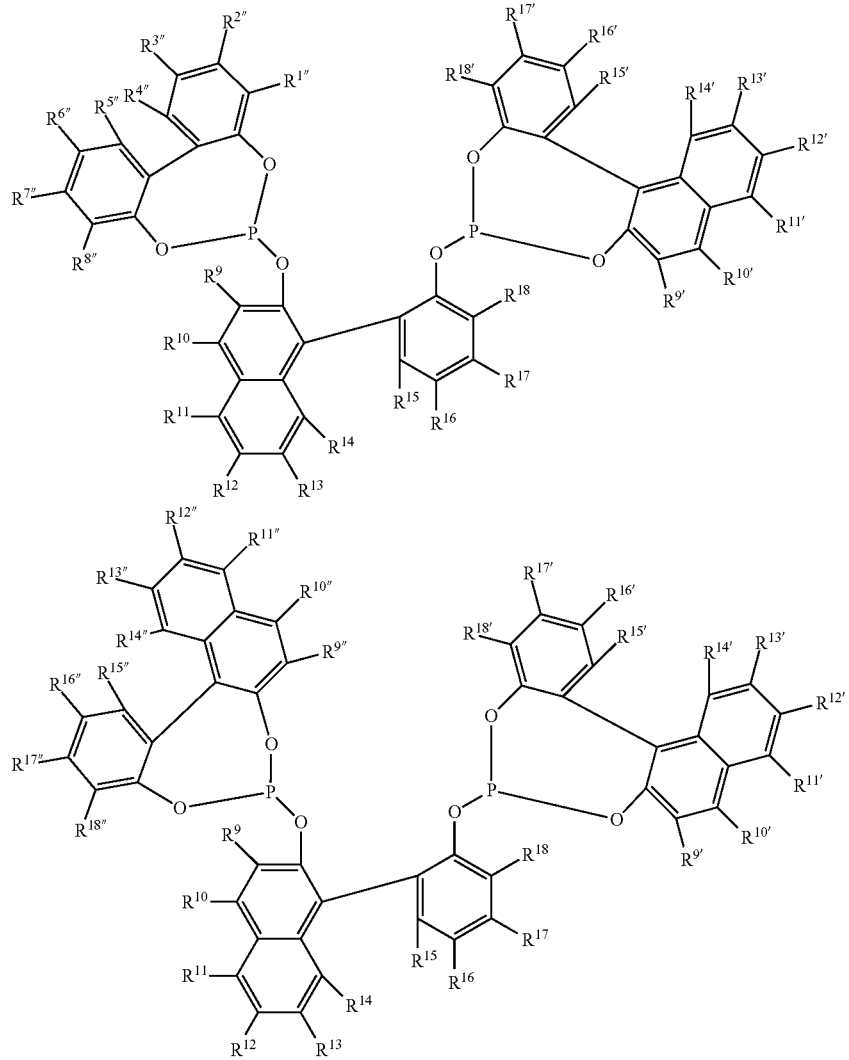

where
$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$, are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —SO$_3$H, —CN, —NH$_2$, —N[($C_1$-$C_{12}$)-alkyl]$_2$;
$R^{1'}, R^{2'}, R^{3'}, R^{4'}, R^{5'}, R^{6'}, R^{7'}, R^{8'}, R^{9'}, R^{10'}, R^{11'}, R^{12'}, R^{13'}, R^{14'}, R^{15'}, R^{16'}, R^{17'}, R^{18'}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —COOH, —OH, —SO$_3$H, —CN, —NH$_2$, —N[($C_1$-$C_{12}$)-alkyl]$_2$;
$R^{1''}, R^{2''}, R^{3''}, R^{4''}, R^{5''}, R^{6''}, R^{7''}, R^{8''}, R^{9''}, R^{10''}, R^{11''}, R^{12''}, R^{13''}, R^{14''}, R^{15''}, R^{16''}, R^{17''}, R^{18''}$ are selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, —S-alkyl, —S-aryl, halogen, COO—($C_1$-$C_{12}$)-alkyl, CONH—($C_1$-$C_{12}$)-alkyl, —CO—($C_1$-$C_{12}$)-alkyl, —CO—($C_6$-$C_{20}$)-aryl, —OH, —SO$_3$H, —NH$_2$, —N[($C_1$-$C_{12}$)-alkyl]$_2$;
where the alkyl and aryl groups mentioned may be substituted.

($C_1$-$C_{12}$)-Alkyl and —O—($C_1$-$C_{12}$)-alkyl may each be unsubstituted or substituted by one or more identical or different radicals selected from ($C_3$-$C_{12}$)-cycloalkyl, ($C_3$-$C_{12}$)-heterocycloalkyl, ($C_6$-$C_{20}$)-aryl, fluorine, chlorine, cyano, formyl, acyl and alkoxycarbonyl.

($C_6$-$C_{20}$)-Aryl and —($C_6$-$C_{20}$)-aryl-($C_6$-$C_{20}$)-aryl- may each be unsubstituted or substituted by one or more identical or different radicals selected from:
—H, —($C_1$-$C_{12}$)-alkyl, —O—($C_1$-$C_{12}$)-alkyl, —O—($C_6$-$C_{20}$)-aryl, —($C_6$-$C_{20}$)-aryl, -halogen (such as Cl, F, Br, I), —COO—($C_1$-$C_{12}$)-alkyl, —CONH—($C_1$-$C_{12}$)-alkyl, —($C_6$-$C_{20}$)-aryl-CON[($C_1$-$C_{12}$)-alkyl]$_2$, —CO—($C_1$-$C_{12}$)-alkyl, —CO—($C_6$-$C_{20}$)-aryl, —COOH, —OH, —SO$_3$H; —SO$_3$Na, —NO$_2$, —CN, —NH$_2$, —N[($C_1$-$C_{12}$)-alkyl]$_2$.

In the context of the invention, the expression "—($C_1$-$C_{12}$)-alkyl" encompasses straight-chain and branched alkyl groups. Preferably, these groups are unsubstituted straight-chain or branched —($C_1$-$C_8$)-alkyl groups and most preferably —($C_1$-$C_6$)-alkyl groups. Examples of —($C_1$-$C_{12}$)-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression "—$(C_1-C_{12})$-alkyl" also apply to the alkyl groups in —O—$(C_1-C_{12})$-alkyl, i.e. in —$(C_1-C_{12})$-alkoxy. Preferably, these groups are unsubstituted straight-chain or branched —$(C_1-C_6)$-alkoxy groups.

Substituted —$(C_1-C_{12})$-alkyl groups and substituted —$(C_1-C_{12})$-alkoxy groups may have one or more substituents, depending on their chain length. The substituents are preferably each independently selected from —$(C_3-C_{12})$-cycloalkyl, —$(C_3-C_{12})$-heterocycloalkyl, —$(C_6-C_{20})$-aryl, fluorine, chlorine, cyano, formyl, acyl and alkoxycarbonyl.

The expression "—$(C_3-C_{12})$-cycloalkyl", in the context of the present invention, encompasses mono-, bi- or tricyclic hydrocarbyl radicals having 3 to 12, especially 5 to 12, carbon atoms. These include cyclopropyl, cyclobutyl, cyclopentyl, cyclohexyl, cycloheptyl, cyclooctyl, cyclododecyl, cyclopentadecyl, norbornyl and adamantyl. One example of a substituted cycloalkyl would be menthyl.

The expression "—$(C_3-C_{12})$-heterocycloalkyl groups", in the context of the present invention, encompasses nonaromatic saturated or partly unsaturated cycloaliphatic groups having 3 to 12, especially 5 to 12, carbon atoms. The —$(C_3-C_{12})$-heterocycloalkyl groups have preferably 3 to 8, more preferably 5 or 6, ring atoms. In the heterocycloalkyl groups, as opposed to the cycloalkyl groups, 1, 2, 3 or 4 of the ring carbon atoms are replaced by heteroatoms or heteroatom-containing groups. The heteroatoms or the heteroatom-containing groups are preferably selected from —O—, —S—, —N—, —N(=O)—, —C(=O)— and —S(=O)—. Examples of —$(C_3-C_{12})$-heterocycloalkyl groups are tetrahydrothiophenyl, tetrahydrofuryl, tetrahydropyranyl and dioxanyl.

In the context of the present invention, the expression "—$(C_6-C_{20})$-aryl and —$(C_6-C_{20})$-aryl-$(C_6-C_{20})$-aryl-" encompasses mono- or polycyclic aromatic hydrocarbyl radicals. These have 6 to 20 ring atoms, more preferably 6 to 14 ring atoms, especially 6 to 10 ring atoms. Aryl is preferably —$(C_6-C_{10})$-aryl and —$(C_6-C_{10})$-aryl-$(C_6-C_{10})$-aryl-. Aryl is especially phenyl, naphthyl, indenyl, fluorenyl, anthracenyl, phenanthrenyl, naphthacenyl, chrysenyl, pyrenyl, coronenyl. More particularly, aryl is phenyl, naphthyl and anthracenyl.

Substituted —$(C_6-C_{20})$-aryl groups and —$(C_6-C_{20})$-aryl-$(C_6-C_{20})$-aryl groups may have one or more (e.g. 1, 2, 3, 4 or 5) substituents, depending on the ring size. These substituents are preferably each independently selected from —H, —$(C_1-C_{12})$-alkyl, —O—$(C_1-C_{12})$-alkyl, —O—$(C_6-C_{20})$-aryl, —$(C_6-C_{20})$-aryl, -halogen (such as Cl, F, Br, I), —COO—$(C_1-C_{12})$-alkyl, —CONH—$(C_1-C_{12})$-alkyl, —$(C_6-C_{20})$-aryl-CON[$(C_1-C_{12})$-alkyl]$_2$, —CO—$(C_1-C_{12})$-alkyl, —CO—$(C_6-C_{20})$-aryl, —COOH, —OH, —SO$_3$H, —SO$_3$Na, —NO$_2$, —CN, —NH$_2$, —N[$(C_1-C_{12})$-alkyl]$_2$.

Substituted —$(C_6-C_{20})$-aryl groups and —$(C_6-C_{20})$-aryl-$(C_6-C_{20})$-aryl groups are preferably substituted —$(C_6-C_{10})$-aryl groups and —$(C_6-C_{10})$-aryl-$(C_6-C_{10})$-aryl groups, especially substituted phenyl or substituted naphthyl or substituted anthracenyl. Substituted —$(C_6-C_{20})$-aryl groups preferably bear one or more, for example 1, 2, 3, 4 or 5, substituents selected from —$(C_1-C_{12})$-alkyl groups, —$(C_1-C_{12})$-alkoxy groups.

In one embodiment, $R^1$, $R^2$, $R^3$, $R^4$, $R^5$, $R^6$, $R^7$, $R^8$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^{1'}$, $R^{2'}$, $R^{3'}$, $R^{4'}$, $R^{5'}$, $R^{6'}$, $R^{7'}$, $R^{8'}$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^{1''}$, $R^{2''}$, $R^{3''}$, $R^{4''}$, $R^{5''}$, $R^{6''}$, $R^{7''}$, $R^{8''}$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^{9'}$, $R^{10'}$, $R^{11'}$, $R^{12'}$, $R^{13'}$, $R^{14}$, $R^{15'}$, $R^{16'}$, $R^{17'}$, $R^{18'}$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^{9'}$, $R^{10'}$, $R^{11'}$, $R^{12'}$, $R^{13}$, $R^{14'}$, $R^{15'}$, $R^{16'}$, $R^{17'}$, $R^{18'}$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^{9''}$, $R^{10''}$, $R^{11''}$, $R^{12''}$, $R^{13''}$, $R^{14''}$, $R^{15''}$, $R^{16''}$, $R^{17''}$, $R^{18''}$ are selected from:
—H, —$(C_1-C_{12})$-alkyl, —O—$(C_1-C_{12})$-alkyl, —O—$(C_6-C_{20})$-aryl, —S-alkyl, —S-aryl.

In one embodiment, $R^1$, $R^2$, $R^3$, $R^4$, $R^5$, $R^6$, $R^7$, $R^8$ are selected from:
—H, —$(C_1-C_{12})$-alkyl, —O—$(C_1-C_{12})$-alkyl, —O—$(C_6-C_{20})$-aryl.

In one embodiment, $R^{1'}$, $R^{2'}$, $R^{3'}$, $R^{4'}$, $R^{5'}$, $R^{6'}$, $R^{7'}$, $R^{8'}$ are selected from:
—H, —$(C_1-C_{12})$-alkyl, —O—$(C_1-C_{12})$-alkyl, —O—$(C_6-C_{20})$-aryl.

In one embodiment, $R^{1''}$, $R^{2''}$, $R^{3''}$, $R^{4''}$, $R^{5''}$, $R^{6''}$, $R^{7''}$, $R^{8''}$ are selected from:
—H, —$(C_1-C_{12})$-alkyl, —O—$(C_1-C_{12})$-alkyl, —O—$(C_6-C_{20})$-aryl.

In one embodiment, $R^{9''}$, $R^{10''}$, $R^{11''}$, $R^{12''}$, $R^{13''}$, $R^{14''}$, $R^{15''}$, $R^{16''}$, $R^{17''}$, $R^{18''}$ are selected from:
—H, —$(C_1-C_{12})$-alkyl, —O—$(C_1-C_{12})$-alkyl, —O—$(C_6-C_{20})$-aryl.

In one embodiment, $R^{9'}$, $R^{10'}$, $R^{11'}$, $R^{12'}$, $R^{13'}$, $R^{14'}$, $R^{15'}$, $R^{16'}$, $R^{17}$, $R^{18'}$ are selected from:
—H, —$(C_1-C_{12})$-alkyl, —O—$(C_1-C_{12})$-alkyl, —O—$(C_6-C_{20})$-aryl.

In one embodiment, $R^{9''}$, $R^{10''}$, $R^{11''}$, $R^{12''}$, $R^{13''}$, $R^{14''}$, $R^{15''}$, $R^{16''}$, $R^{17''}$, $R^{18''}$ are selected from:
—H, —$(C_1-C_{12})$-alkyl, —O—$(C_1-C_{12})$-alkyl, —O—$(C_6-C_{20})$-aryl.

In one embodiment, the compound has the general structure (I).

In one embodiment, the compound has the general structure (II).

In one embodiment, the compound has the general structure (III).

In one embodiment, the compound has the general structure (IV).

The invention is illustrated in detail hereinafter by working examples and a FIGURE.

FIG. 1 shows a reaction apparatus in which the coupling reaction to give the corresponding unsymmetric biaryls can be conducted. The apparatus comprises a nickel cathode (1) and an anode composed of boron-doped diamond (BDD) on silicon (5). The apparatus can be cooled with the aid of a cooling jacket (3). The arrows indicate the flow direction of the cooling water. The reaction space is sealed by a Teflon stopper (2). The reaction mixture is mixed by a magnetic stirrer bar (7). On the anodic side, the apparatus is sealed by screw clamps (4) and seals (6).

ANALYSIS

Chromatography

The preparative liquid chromatography separations via flash chromatography were conducted with a maximum pressure of 1.6 bar on 60 M silica gel (0.040-0.063 mm) from Macherey-Nagel GmbH & Co, Düren. The unpressurized separations were conducted on Geduran Si 60 silica gel (0.063-0.200 mm) from Merck KGaA, Darmstadt. The solvents used as eluents (ethyl acetate (technical grade), cyclohexane (technical grade)) had been purified by distillation beforehand on a rotary evaporator.

For thin-film chromatography (TLC), ready-made PSC silica gel 60 F254 plates from Merck KGaA, Darmstadt were used. The Rf values are reported as a function of the eluent mixture used. The TLC plates were stained using a cerium/molybdatophosphoric acid solution as immersion reagent. Cerium/molybdatophosphoric acid reagent: 5.6 g of molybdatophosphoric acid, 2.2 g of cerium(IV) sulphate tetrahydrate and 13.3 g of concentrated sulphuric acid to 200 ml of water.

Gas Chromatography (GC/GCMS)

The gas chromatography studies (GC) on product mixtures and pure substances were effected with the aid of the GC-2010 gas chromatograph from Shimadzu, Japan. Analysis is effected on an HP-5 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, end temperature 290° C. for 8 min). Gas chromatography-mass spectrometry analyses (GC-MS) of product mixtures and pure substances were recorded with the aid of the GC-2010 gas chromatograph combined with the GCMS-QP2010 mass detector from Shimadzu, Japan. Analysis is effected on an HP-1 quartz capillary column from Agilent Technologies, USA (length: 30 m; internal diameter: 0.25 mm; film thickness of the covalently bound stationary phase: 0.25 μm; carrier gas: hydrogen; injector temperature: 250° C.; detector temperature: 310° C.; programme: "hard" method: start temperature 50° C. for 1 min, heating rate: 15° C./min, end temperature 290° C. for 8 min; GC-MS: ion source temperature: 200° C.).

Melting Points

Melting points were measured with the aid of the SG 2000 melting point determination instrument from HW5, Mainz, and are uncorrected.

Elemental Analysis

The elemental analyses were conducted in the analytical division of the Organic Chemistry department of the Johannes Gutenberg University of Mainz on a Vario EL Cube from Foss-Heraeus, Hanau.

Mass Spectrometry

All electrospray ionization analyses (ESI+) were conducted on a QTof Ultima 3 from Waters Micromasses, Milford, Mass. EI mass spectra and the high-resolution EI spectra were analysed on an instrument of the MAT 95 XL sector field instrument type from ThermoFinnigan, Bremen.

NMR Spectroscopy

The NMR spectroscopy studies were conducted on multinucleus resonance spectrometers of the AC 300 or AV II 400 type from Bruker, Analytische Messtechnik, Karlsruhe. The solvent used was CDCl3. The 1H and 13C spectra were calibrated according to the residual content of undeuterated solvent using the NMR Solvent Data Chart from Cambridge Isotopes Laboratories, USA. Some of the 1H and 13C signals were assigned with the aid of H,H-COSY, H,H-NOESY, H,C-HSQC and H,C-HMBC spectra. The chemical shifts are reported as δ values in ppm. For the multiplicities of the NMR signals, the following abbreviations were used: s (singlet), bs (broad singlet), d (doublet), t (triplet), q (quartet), m (multiplet), dd (doublet of doublets), dt (doublet of triplets), tq (triplet of quartets). All coupling constants J were reported in hertz (Hz) together with the number of bonds covered. The numbering given in the assignment of signals corresponds to the numbering shown in the formula schemes, which do not necessarily have to correspond to IUPAC nomenclature.

General Operating Procedures

All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Synthesis of Unsymmetric Biaryls

The unsymmetric biaryls were prepared by an electrochemical method by coupling two phenols or one naphthol and one phenol which differ in terms of oxidation potential. In this regard, see also B. Elsler, D. Schollmeyer, K. M. Dyballa, R. Franke, S. R. Waldvogel, "Metall- und reagensfreie hochselektive anodische Kreuzkupplung von Phenolen" [Metal- and Reagent-Free High-Selectivity Anodic Cross-Coupling of Phenols], Angew. Chem., 2014, DOI: 10.1002/ange.201400627

General Procedure:

The coupling reaction was conducted in an apparatus as shown in FIG. 1.

5 mmol of the first phenol having an oxidation potential $E_{Ox}1$ together with 15 mmol of the second phenol having an oxidation potential $E_{Ox}2$ are dissolved in 1,1,1,3,3,3-hexafluoroisopropanol (HFIP) and MeOH or in formic acid and MeOH in the amounts specified in Table 1 below. The electrolysis is galvanostatic.

The outer shell of the electrolysis cell is kept at a controlled temperature of about 10° C. by means of a thermostat, while the reaction mixture is stirred and heated to 50° C. with the aid of a sand bath. After the electrolysis has ended, the cell contents are transferred together with toluene to a 50 ml round-bottom flask and the solvent is removed on a rotary evaporator at 50° C., 200-70 mbar, under reduced pressure. Unconverted reactant is recovered by means of short-path distillation (100° C., $10^{-3}$ mbar).

Electrode Material

Anode: boron-doped diamond (BDD) on Si

Cathode: Ni mesh

Electrolysis Conditions:

Temperature [T]: 50° C.

Current [I]: 15 mA

Current density [j]: 2.8 mA/cm$^2$

Charge [Q]: 2 F/mol of deficiency component

Terminal voltage [$U_{max}$]: 3-5 V

The biaryls were synthesized by the general method described above, and in a reaction apparatus as shown in FIG. 1.

2,2'-Dihydroxy-4',5-dimethyl-5'-(methylethyl)-3-methoxybiphenyl

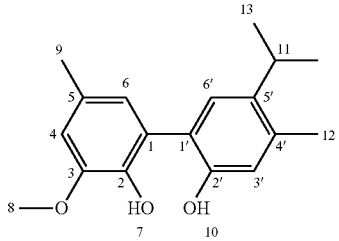

0.69 g (5 mmol, 1.0 equiv.) of 4-methylguaiacol and 2.28 g (15 mmol, 3.0 equiv.) of 3-methyl-4-(methylethyl)phenol were dissolved in 33 ml of HFIP, 0.68 g of methyltriethylammonium methylsulphate (MTES) were added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 716 mg (50%, 2.5 mmol)
GC (hard method, HP-5): $t_R$=14.87 min
$R_f$(CH:EA=4:1)=0.43
$m_p$=126.8° C. (recrystallized from CH)
$^1$H NMR (600 MHz, DMSO) δ=1.17-1.12 (m, 6H, 13-H), 2.24 (m, 6H, 9-H/12-H), 3.01 (dt, 1H, 11-H), 3.79 (s, 3H, 8-H), 6.55 (s, 1H, 6-H), 6.66 (d, 1H, 6'-H), 6.73 (d, 1H, 4-H), 6.96 (s, 1H, 3'-H), 8.16 (s, 1H, 7-H), 8.84 (s, 1H, 10-H);
Couplings: $^4J_{4\text{-}H,\ 6\text{-}H}$=2.2 Hz, $^4J_{6'\text{-}H,\ 11\text{-}H}$=2.9 Hz, $^3J_{11\text{-}H,\ 13\text{-}H}$=6.8 Hz;
$^{13}$C NMR (151 MHz, DMSO) δ=18.73, 20.80 (C-9/C-12), 23.54 (C-13), 28.10 (C-11), 55.78 (C-8), 111.23 (C-4), 117.34 (C-6'), 123.42 (C-1'), 123.49 (C-6), 126.43 (C-1), 127.36 (C-5), 127.49 (C-3'), 134.40 (C-5'), 136.62 (C-4'), 141.12 (C-2), 147.65 (C-3), 151.69 (C-2').
HRMS for $C_{18}H_{22}O_3$ (ESI+) [M+Na$^+$]: calc: 309.1467. found: 309.1457.
MS (EI, GCMS): m/z (%): 286 (50) [M]$^+$, 271 (100) [M-CH$_3$]$^+$, 244 (22) [M-C$_3$H$_6$]$^+$.
Elemental analysis for $C_{18}H_{22}O_3$: calc: C, 75.50%; H, 7.74%. found: C, 75.01%; H, 7.70%.

2,2'-Dihydroxy-5,5'-dimethyl-3-methoxybiphenyl

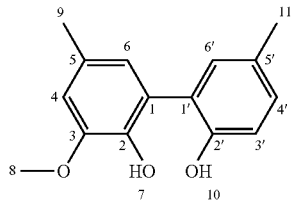

1.66 g (12 mmol, 1.0 equiv.) of 4-methylguaiacol and 3.91 g (36 mmol, 3.0 equiv.) of 4-methylphenol were dissolved in 65 ml of HFIP and 14 ml of MeOH, 1.63 g of methyltriethylammonium methylsulphate (MTES) were added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 440 mg (36%, 1.8 mmol)
GC (hard method, HP-5): $t_R$=13.56 min
$R_f$(CH:EA=4:1)=0.38
$m_p$=162.0° C. (recrystallized from CH)
$^1$H NMR (400 MHz, DMSO) δ=2.18 (s, 3H, 9-H/11-H), 2.21 (s, 3H, 9-H/11-H), 3.76 (s, 3H, 8-H), 6.53 (s, 1H, 6-H), 6.71 (s, 1H, 4-H), 6.75 (d, 1H, 3'-H), 6.86-6.94 (m, 2H, 4'-H/6'-H), 8.53 (bs, 1H, 7-H/12-H);
Couplings: $^3J_{3'\text{-}H,\ 4'\text{-}H}$=8.4 Hz;
$^{13}$C NMR (101 MHz, DMSO) δ=20.21, 20.77 (C-9/C-11), 55.79 (C-8), 111.36 (C-4), 115.69 (C-3'), 123.50 (C-6), 125.72 (C-1'), 126.16 (C-1), 127.20 (C-5), 127.30 (C-5'), 128.50 (C-6'), 131.83 (C-4'), 141.20 (C-2), 147.61 (C-3), 152.11 (C-2').
HRMS for $C_{15}H_{16}O_3$(ESI+) [M+Na$^+$]: calc: 267.0997. found: 267.0999.
MS (EI, GCMS): m/z (%): 244 (100) [M]$^+$, 229 (64) [M-CH$_3$]$^+$.
Elemental analysis for $C_{15}H_{16}O_3$: calc: C, 73.75%; H, 6.60%. found: C, 73.81%; H, 6.54%.

2,2'-Dihydroxy-3-methoxy-3',5,5'-trimethylbiphenyl

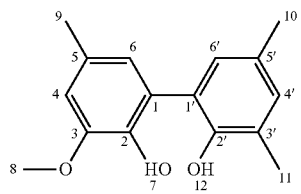

0.70 g (6 mmol, 1.0 equiv.) of 4-methylguaiacol and 2.08 g (17 mmol, 3.0 equiv.) of 2,4-dimethylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a pale yellow solid.

Yield: 663 mg (45%, 2.5 mmol)
GC (hard method, HP-5): $t_R$=13.97 min
$R_f$(CH:EA=4:1)=0.29
$m_p$=119.7° C. (recrystallized from DCM/CH)
$^1$H NMR (400 MHz, CDCl$_3$) δ=2.34 (s, 3H, 10-H), 2.35 (s, 3H, 11-H), 2.38 (s, 3H, 9-H), 3.94 (s, 3H, 8-H), 6.16 (s, 1H, 12-H), 6.20 (s, 1H, 7-H), 6.76 (d, 1H, 4-H), 6.78 (d, 1H, 6-H), 6.98 (d, 1H, 6'-H), 7.03 (d, 1H, 4'-H);
Couplings: $^4J_{4\text{-}H,\ 6\text{-}H}$=1.7 Hz, $^4J_{4'\text{-}H,\ 6'\text{-}H}$=2.1 Hz;
$^{13}$C NMR (101 MHz, CDCl$_3$) δ=16.51 (C-9), 20.54 (C-10), 21.20 (C-11), 56.12 (C-8), 110.92 (C-4), 123.95 (C-6), 124.13 (C-1), 124.64 (C-1'), 126.18 (C-3'), 128.82 (C-6'), 129.59 (C-5'), 130.40 (C-5), 131.40 (C-4'), 139.46 (C-2), 146.35 (C-3), 149.42 (C-2').
HRMS for $C_{18}H_{16}O_3$(ESI+) [M+Na$^+$]: calc: 281.1154. found: 281.1152.
MS (EI, GCMS): m/z (%): 242 (100) [M]$^+$, 227 (38) [M-CH$_3$]$^+$.

Elemental analysis for $C_{16}H_{18}O_3$: calc: C, 68.31%; H, 6.45%. found: C, 68.29%; H, 6.40%.

2,2'-Dihydroxy-3-methoxy-5-methyl-4'-(dimethylethyl)biphenyl

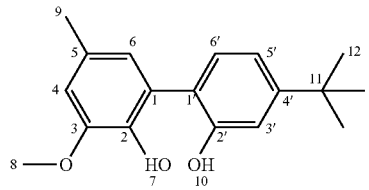

0.69 g (5 mmol, 1.0 equiv.) of 4-methylguaiacol and 2.25 g (15 mmol, 3.0 equiv.) of 3-tert-butylphenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a colourless solid.

Yield: 808 mg (63%, 3.1 mmol)
GC (hard method, HP-5): $t_R$=13.97 min
$R_f$(CH:EA=4:1)=0.29
$m_p$=160.3° C. (recrystallized from DCM/CH)
$^1$H NMR (400 MHz, CDCl$_3$) δ=1.37 (s, 9H, 12-H), 2.36 (s, 3H, 9-H), 3.94 (s, 3H, 8-H), 6.25 (s, 1H, 7-H), 6.48 (s, 1H, 10-H), 6.75 (d, 1H, 6-H), 6.79 (d, 1H, 4-H), 7.08 (dd, 1H, 5'-H), 7.12 (d, 1H, 3'-H), 7.27 (d, 1H, 6'-H);
Couplings: $^4J_{4\text{-}H,\ 6\text{-}H}$=1.7 Hz; $^3J_{5'\text{-}H,\ 6'\text{-}H}$=8.0 Hz, $^4J_{3'\text{-}H,\ 5'\text{-}H}$=1.7 Hz;
$^{13}$C NMR (101 MHz, CDCl$_3$) δ=21.24 (C-9), 31.31 (C-12), 34.58 (C-11), 56.15 (C-8), 110.79 (C-4), 114.94 (C-3'), 118.30 (C-5'), 122.37 (C-1'), 123.88 (C-1), 123.94 (C-6), 130.45 (C-6'), 130.53 (C-4'), 139.24 (C-5), 146.32 (C-3), 152.91 (C-2'), 153.13 (C-2).
HRMS for $C_{15}H_{16}O_4$(ESI+) [M+Na$^+$]: calc: 309.1467. found: 309.1466.
MS (EI, GCMS): m/z (%): 242 (100) [M]$^+$, 227 (38) [M-CH$_3$]$^+$.
Elemental analysis for $C_{18}H_{22}O_3$: calc: 75.50%; H, 7.74%. found: C, 75.41%; H, 7.72%.

2,2'-Dihydroxy-4',5-dimethyl-3-methoxylbiphenyl 0.70 g (5 mmol, 1.0 equiv.) of 4-methylguaiacol and 1.65 g (15 mmol, 3.0 equiv.) of 3-methylphenol were dissolved in 33 ml of HFIP, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and two cross-coupling products are obtained as colourless solids.

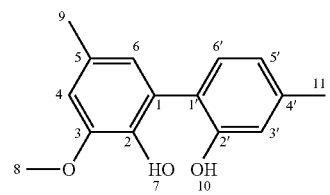

Yield: 266 mg (21%, 1.1 mmol)
GC (hard method, HP-5): $t_R$=13.72 min
$R_f$(CH:EA=4:1)=0.25
$m_p$=136.2° C. (recrystallized from DCM/CH)
$^1$H NMR (400 MHz, CDCl$_3$) δ=2.35 (s, 3H, 9-H/11-H), 2.37 (s, 3H, 9-H/11-H), 3.94 (s, 3H, 8-H), 6.17 (s, 1H, 10-H), 6.35 (s, 1H, 2-H), 6.74 (d, 1H, 4-H), 6.76 (s, 1H, 6-H), 6.88-6.83 (m, 1H, 5'-H), 6.90 (d, 1H, 3'-H), 7.21 (d, 1H, 6'-H);
Couplings: $^4J_{4\text{-}H,\ 6\text{-}H}$=1.8 Hz, $^3J_{5'\text{-}H,\ 6'\text{-}H}$=7.7 Hz, $^4J_{3'\text{-}H,\ 5'\text{-}H}$=1.5 Hz;
$^{13}$C NMR (101 MHz, CDCl$_3$) δ=21.11, 21.20 (C-9/C-11), 56.13 (C-8), 110.81 (C-4), 118.25 (C-3'), 121.97 (C-5'), 122.39 (C-1), 123.77 (C-1'), 123.85 (C-6), 130.50 (C-5), 130.68 (C-6'), 139.30 (C-4'), 139.54 (C-2), 146.31 (C-3), 153.33 (C-2').
HRMS for $C_{15}H_{16}O_3$(ESI+) [M+Na$^+$]: calc: 267.0997. found: 267.1006.
MS (EI, GCMS): m/z (%): 244 (100) [M]$^+$, 229 (18) [M-CH$_3$]$^+$.
Elemental analysis for $C_{15}H_{16}O_3$: calc: C, 73.75%; H, 6.60%. found: C, 73.70%; H, 6.68%.

2,2'-Dihydroxy-3-methoxy-4'-5,5'-trimethylbiphenyl

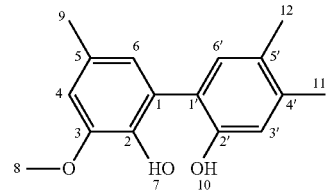

0.69 g (5 mmol, 1.0 equiv.) of 4-methylguaiacol and 1.83 g (15 mmol, 3.0 equiv.) of 3,4-dimethylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 688 mg (52%, 2.6 mmol)
GC (hard method, HP-5): $t_R$=14.52 min
$R_f$(CH:EA=4:1)=0.29
$m_p$=152.3° C. (recrystallized from DCM/CH)
$^1$H NMR (400 MHz, CDCl$_3$) δ=12.25 (s, 3H, 11-H), 2.28 (s, 3H, 12-H), 2.36 (s, 3H, 9-H), 3.93 (s, 3H, 8-H), 6.19 (s, 1H, 7-H), 6.25 (s, 1H, 10-H), 6.73 (d, 1H, 4-H), 6.76 (s, 1H, 6-H), 6.88 (s, 1H, 3'-H), 7.08 (s, 1H, 6'-H);
Couplings: $^4J_{4\text{-}H,\ 6\text{-}H}$=1.7 Hz;

$^{13}$C NMR (101 MHz, CDCl$_3$) δ=18.89 (C-11), 19.60 (C-12), 21.24 (C-9), 56.14 (C-8), 110.74 (C-4), 118.93 (C-3'), 122.54 (C-1), 123.82 (C-6), 123.97 (C-1'), 129.03 (C-5), 130.46 (C-4'), 131.69 (C-6'), 137.94 (C-5'), 139.26 (C-2), 146.31 (C-3), 151.36 (C-2').

HRMS for C$_{16}$H$_{18}$O$_3$(ESI+) [M+Na$^+$]: calc: 281.1154. found: 281.1157.

MS (EI, GCMS): m/z (%): 258 (100) [M]$^+$, 243 (10) [M-CH$_3$]$^+$.

Elemental analysis for C$_{16}$H$_{18}$O$_3$: calc: 74.39%; H, 7.02%. found: C, 74.32%; H, 7.20%.

2,2'-Dihydroxy-5'-isopropyl-3-methoxy-5-methylbiphenyl

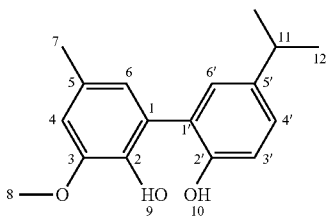 [SMILES: COc1cc(C)cc(-c2cc(C(C)C)ccc2O)c1O]

0.69 g (5 mmol, 1.0 equiv.) of 4-methylguaiacol and 2.05 g (15 mmol, 3.0 equiv.) of 4-isopropylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil.

Yield: 0.53 g (39%, 1.9 mmol).

GC (hard method, HP-5): t$_R$=14.23 min

R$_f$(CH:EA=4:1)=0.30

$^1$H NMR (400 MHz, CDCl$_3$) δ=1.27 (m, 6H), 2.36 (s, 3H), 2.91 (dt, J=13.8, 6.9, 6.9 Hz, 1H), 3.94 (s, 3H), 6.13-6.27 (m, 2H), 6.82-6.65 (m, 1H), 6.25 (m, 2H), 6.75 (s, 1H), 6.77 (s, 1H), 6.99 (d, J=8.1 Hz, 1H), 7.19-7.12 (m, 2H);

$^{13}$C NMR (101 MHz, CDCl$_3$) δ=21.25, 24.27, 33.40, 56.18, 110.92, 117.60, 123.91, 124.23, 125.07, 127.29, 128.80, 130.57, 139.29, 141.42, 146.31, 151.51.

HRMS for C$_{17}$H$_{20}$O$_3$(ESI+) [M+Na$^+$]: calc: 295.1310. found: 295.1297.

MS (EI, GCMS): m/z (%): 272 (80) [M]$^+$, 257 (100) [M-CH$_3$]$^+$.

2,2'-Dihydroxy-3-methoxy-5-methyl-5'-tert-butylbiphenyl

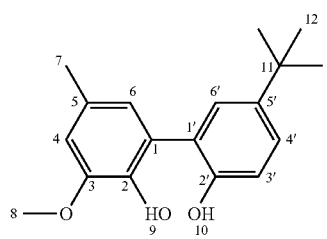

0.69 g (5 mmol, 1.0 equiv.) of 4-methylguaiacol and 2.26 g (15 mmol, 3.0 equiv.) of 4-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellowish oil.

Yield: 0.48 g (34%, 1.7 mmol)

GC (hard method, HP-5): t$_R$=14.52 min

R$_f$(CH:EA=4:1)=0.24

$^1$H NMR (400 MHz, CDCl$_3$) δ=1.34 (s, 9H), 2.37 (s, 3H), 3.94 (s, 3H), 6.17 (s, 1H), 6.24 (s, 1H), 6.75 (s, 1H), 6.77 (s, 1H), 6.99 (d, J=8.4 Hz, 1H), 7.31-7.29 (m, 1H), 7.33 (dd, J=8.4, 2.5 Hz, 1H).

$^{13}$C NMR (101 MHz, CDCl$_3$) δ=21.28, 31.61, 34.20, 56.18, 110.91, 117.25, 123.92, 124.41, 124.63, 126.38, 127.78, 130.58, 139.32, 143.70, 146.32, 151.22.

HRMS for C$_{18}$H$_{22}$O$_3$(ESI+) [M+Na$^+$]: calc: 309.1467. found: 309.1476.

MS (EI, GCMS): m/z (%): 286 (28) [M]$^+$, 271 (100) [M-CH$_3$]$^+$.

2,2'-Dihydroxy-3',5'-di-tert-butyl-5-methyl-3-methoxybiphenyl

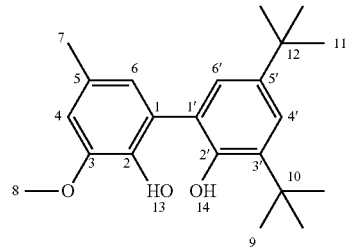 [SMILES: COc1cc(C)cc(-c2cc(C(C)(C)C)cc(C(C)(C)C)c2O)c1O]

0.69 g (5 mmol, 1.0 equiv.) of 4-methylguaiacol and 3.12 g (15 mmol, 3.0 equiv.) of 2,4-di-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 9:1 eluent (cyclohexane:ethyl acetate) and the product is obtained as a colourless solid.

Yield: 0.41 g (24%, 1.2 mmol)

GC (hard method, HP-5): t$_R$=15.15 min

R$_f$(CH:EA=9:1)=0.35 m$_p$=120.2° C. (recrystallized in n-pentane)

$^1$H NMR (400 MHz, CDCl$_3$) δ=1.36 (s, 9H), 1.50 (s, 9H), 2.38 (s, 3H), 3.96 (s, 3H), 6.00 (s, 1H), 6.05 (s, 1H), 6.77 (s, 1H), 7.16 (d, J=2.5 Hz, 1H), 7.39 (d, J=2.5 Hz, 1H).

$^{13}$C NMR (101 MHz, CDCl$_3$) δ=21.23, 29.88, 31.69, 34.40, 35.23, 56.17, 111.03, 123.96, 124.17, 125.09, 125.50, 130.42, 136.73, 139.72, 142.36, 146.45, 149.82.

MS (EI, GCMS): m/z (%): 342 (22) [M]$^+$, 327 (100) [M-CH$_3$]$^+$.

2,2'-Dihydroxy-3',5-dimethyl-3-methoxy-5'-tert-butylbiphenyl

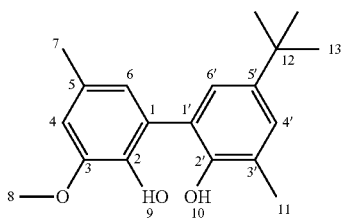 [SMILES: COc1cc(C)cc(-c2cc(C(C)(C)C)cc(C)c2O)c1O]

0.69 g (5 mmol, 1.0 equiv.) of 4-methylguaiacol and 2.47 g (15 mmol, 3.0 equiv.) of 2-methyl-4-tert-butylphenol were dissolved in 27 ml of HFIP and 6 ml of MeOH, 0.68 g of methyltriethylammonium methylsulphate (MTES) was added and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellowish oil.

Yield: 0.69 g (46%, 2.3 mmol)
GC (hard method, HP-5): $t_R$=14.79 min
$R_f$(CH:EA=4:1)=0.33
$^1$H NMR (400 MHz, CDCl$_3$) δ=1.37 (s, 9H), 2.39 (d, J=2.4 Hz, 6H), 3.94 (s, 3H), 6.15 (s, 1H), 6.17 (s, 1H), 6.77 (s, 1H), 6.79 (s, 1H), 7.17 (d, J=2.5 Hz, 1H), 7.24 (d, J=2.4 Hz, 1H);
$^{13}$C NMR (101 MHz, CDCl$_3$) δ=16.90, 21.28, 31.67, 34.12, 56.16, 110.94, 124.02, 124.17, 124.59, 125.41, 125.65, 127.86, 130.47, 139.50, 143.07, 146.40, 149.41.
MS (EI, GCMS): m/z (%): 300 (18) [M]$^+$, 285 (100) [M-CH$_3$]$^+$.

2,2'-Dihydroxy-3-methoxy-5-methyl-5'-(1-methyl-ethyl)biphenyl

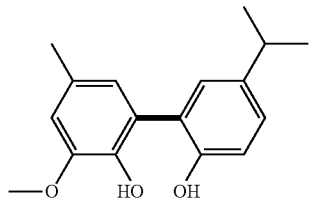

0.69 g (5 mmol, 1.0 eq.) of 4-methylguaiacol and 2.05 g (15 mmol, 3.0 eq.) of 4-isopropylphenol and 0.68 g of methyltriethylammonium methylsulphate (MTES) in 27 ml of HFIP+6 ml of MeOH were added to methyltriethylammonium methylsulphate (MTES) and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil.

Yield: 39%, 527 mg, 1.9 mmol.
$R_f$(cyclohexane:ethyl acetate=4:1)=0.30; $^1$H NMR (400 MHz, CDCl$_3$) δ=1.27 (m, 6H), 2.36 (s, 3H), 2.91 (sept, J=6.9 Hz, 1H), 3.94 (s, 3H), 6.13-6.27 (m, 2H), 6.65-6.82 (m, 2H), 6.99 (d, J=8.1 Hz, 1H), 7.12-7.19 (m, 2H); $^{13}$C NMR (101 MHz, CDCl$_3$) δ=21.37, 24.39, 33.53, 56.31, 111.04, 117.73, 124.04, 124.36, 125.20, 127.42, 128.93, 130.70, 139.42, 141.55, 146.44, 151.64. HRMS for C$_{17}$H$_{20}$O$_3$(ESI+) [M+Na$^+$]: calculated: 295.1310. found: 295.1297; MS (EI, GCMS): m/z (%): 272 (80) [M]$^+$, 257 (100) [M-CH$_3$]$^+$.

2,2'-Dihydroxy-3-methoxy-5-methyl-4'-(methyl-ethyl)biphenyl

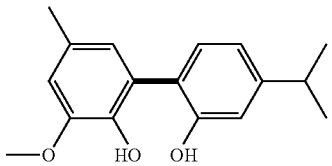

0.69 g (5 mmol, 1.0 eq.) of 4-methylguaiacol and 2.065 g (15 mmol, 3.0 eq.) of 3-isopropylphenol and 0.68 g of methyltriethylammonium methylsulphate (MTES) were dissolved in 33 ml of HFIP and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a brownish oil (yield: 52%, 705 mg, 2.6 mmol).

$R_f$ (cyclohexane:ethyl acetate=4:1)=0.29; $^1$H NMR (400 MHz, CDCl$_3$) δ=1H NMR (400 MHz, CDCl3) δ 1.27 (s, 3H), 1.29 (s, 3H), 2.34 (s, 3H), 2.91 (sept, J=7.0 Hz, 1H), 3.94 (s, 3H), 6.15 (s, 1H), 6.35 (s, 1H), 6.73 (d, J=1.8 Hz, 1H), 6.75-6.77 (m, 1H), 6.90 (dd, J=7.9 Hz, 1.8 Hz, 1H), 6.94 (d, J=1.7 Hz, 1H), 7.23 (d, J=7.8 Hz, 1H). $^{13}$C NMR (101 MHz, CDCl$_3$) δ=21.36, 24.02, 33.92, 56.30, 77.16, 110.91, 115.77, 119.56, 122.81, 124.00, 124.08, 130.65, 130.84, 139.38, 146.43, 150.72, 153.54. HRMS for C$_{17}$H$_{20}$O$_3$(ESI+) [M+Na$^+$]: calculated: 295.1310. found: 295.1305; MS (EI, GCMS): m/z (%): 272 (100) [M]$^+$, 257 (50) [M-CH$_3$]$^+$. Elemental analysis for C$_{17}$H$_{20}$O$_3$: calculated 74.97%; H, 7.40%. found: C, 75.05%; H, 7.36%.

2,2'-Dihydroxy-4',5-dimethyl-3-methoxybiphenyl 0.28 g (2 mmol, 1.0 eq.) of 4-methylguaiacol, 1.22 g (6 mmol, 3.0 eq.) of 3-methylphenol and 0.77 g of MTBS were dissolved in 25 ml of HFIP and the electrolyte was transferred to the beaker-type electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and this led to the two cross-coupling products as a colourless and viscous oil.

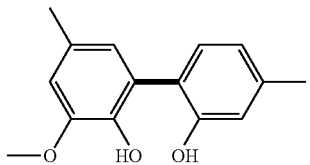

Yield: 21%, 266 mg, 1.1 mmol; $R_f$ (cyclohexane:ethyl acetate=4:1)=0.25; m$_p$=136.2° C. (crystallized from dichloromethane/cyclohexane); $^1$H NMR (400 MHz, CDCl$_3$) δ=2.35 (s, 3H), 2.37 (s, 3H), 3.94 (s, 3H), 6.17 (s, 1H), 6.35 (s, 1H), 6.74 (d, J=1.8 Hz, 1H), 6.76 (s, 1H), 6.88-6.83 (m, 1H), 6.90 (d, 1H, J=1.5 Hz), 7.21 (d, 1H, J=7.7 Hz); $^{13}$C NMR (101 MHz, CDCl$_3$) δ=21.11, 21.20 56.13, 110.81, 118.25, 121.97, 122.39, 123.77, 123.85, 130.50, 130.68, 139.30, 139.54, 146.31, 153.33. HRMS for C$_{15}$H$_{16}$O$_3$(ESI+) [M+Na$^+$]: calculated: 267.0997. found: 267.1006; MS (EI, GCMS): m/z (%): 244 (100) [M]$^+$, 229 (18) [M-CH$_3$]$^+$. Elemental analysis for C$_{15}$H$_{16}$O$_3$: calculated: C, 73.75%; H; 6.60%. found: C, 73.70%; H, 6.68%.

2,2'-Dihydroxy-5,5'-dimethyl-3'-(1,1-dimethylethyl)-3-methoxybiphenyl

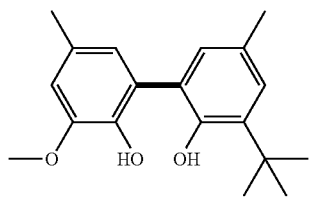

0.69 g (5 mmol, 1.0 eq.) of 4-methylguaiacol, 2.47 g (15 mmol, 3.0 eq.) of 4-methyl-2-tert-butylphenol and 0.68 g of methyltriethylammonium methylsulphate (MTES) were dissolved in 27 ml of HFIP+6 ml of MeOH and the electrolyte was transferred to the electrolysis cell. After the electrolysis, the solvent and unconverted amounts of reactant are removed under reduced pressure, the crude product is purified by flash chromatography on silica gel 60 in a 4:1 eluent (cyclohexane:ethyl acetate) and the product is obtained as a yellow oil (yield: 36%, 545 mg, 1.8 mmol).

$R_f$(cyclohexane:ethyl acetate=9:1)=0.36; $^1$H NMR (400 MHz, CDCl$_3$) δ=1.46 (s, 9H), 2.34 (m, 6H), 3.93 (s, 3H), 5.99 (s, 1H), 6.01 (s, 1H), 6.74 (s, 2H), 6.96 (d, J=1.9 Hz, 1H), 7.14 (d, J=1.9 Hz, 1H); $^{13}$C NMR (101 MHz, CDCl$_3$) δ=21.05, 21.32, 29.96, 35.05, 56.30, 77.16, 111.21, 124.18, 124.24, 125.92, 127.67, 129.15, 129.22, 130.51, 137.57, 139.87, 146.57, 150.10.

HRMS for C$_{22}$H$_{30}$O$_3$(ESI+) [M+Na$^+$]: calculated: 323.1623. found: 323.1618; MS (EI, GCMS): m/z (%): 300 (100) [M]$^+$, 285 (100) [M-CH$_3$]$^+$.

1-(2-Hydroxy-3-methoxy-5-methylphenyl)-2-naphthol

The electrolysis is conducted according to the general procedure in an undivided flange cell with a BDD anode. For this purpose, 0.78 g (5 mmol, 1.0 equiv.) of 2-naphthol and 2.18 g (15 mmol, 3.0 equiv.) of 4-methylguaiacol are dissolved in 27 ml of HFIP and 6 ml of MeOH, 0.68 g of methyltriethylammonium methylsulphate (MTES) is added and the electrolyte is transferred into the electrolysis cell. The solvent and unconverted amounts of reactant are removed under reduced pressure after the electrolysis, the crude product is purified on silica gel 60 in the form of "flash chromatography" in 4:1 eluent (CH:EA) and a product mixture is obtained. A second "flash chromatography" in dichloromethane enables a separation of the two components as a pale red crystalline main product and a colourless crystalline by-product.

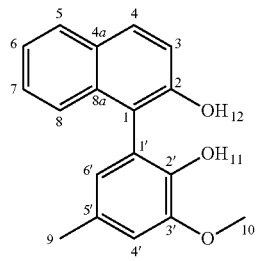

Yield: 899 mg (61%, 3.2 mmol)
GC (hard method, HP-5): $t_R$=15.77 min
$R_f$(CH:EA=4:1)=0.36, $R_f$(DCM)=0.36
$m_p$=145.5° C. (recrystallized from DCM/CH)
$^1$H NMR (400 MHz, CDCl$_3$) δ=2.39 (s, 3H, 9-H), 3.96 (s, 3H, 10-H), 5.47-5.52 (m, 1H, 12-H), 5.65-5.69 (m, 1H, 11-H), 6.75 (d, 1H, 6'-H), 6.85 (d, 1H, 4'-H), 7.32 (dd, 1H, 3-H), 7.34-7.43 (m, 2H, 6-H/7-H), 7.51 (d, 1H, 8-H), 7.83 (s, 1H, 5-H), 7.85 (d, 1H, 4-H);

Couplings: $^3J_{3\text{-}H,\ 4\text{-}H}$=9.0 Hz, $^3J_{7\text{-}H,\ 8\text{-}H}$=8.3 Hz, $^4J_{4'\text{-}H,\ 6'\text{-}H}$=1.8 Hz;
$^{13}$C NMR (101 MHz, CDCl$_3$) δ=21.22 (C-9), 56.08 (C-10), 112.06 (C-4'), 116.62 (C-1), 117.81 (C-3), 119.33 (C-1'), 123.36 (C-6/C-7), 124.42 (C-6'), 124.86 (C-8), 126.48 (C-6/C-7), 128.15 (C-4), 129.18 (C-4a), 129.83 (C-5), 130.36 (C-5'), 133.16 (C-8a), 141.72 (C-2'), 147.24 (C-3'), 150.84 (C-2).

HRMS for C$_{18}$H$_{16}$O$_3$(ESI+) [M+Na$^+$]: calc.: 303.0997. found: 303.1003.
MS (EI, GCMS): m/z (%): 280 (100) [M]$^+$, 265 (12) [M-CH$_3$]$^+$, 249 (12) [M-OCH$_3$]$^+$.
Elemental analysis for C$_{18}$H$_{16}$O$_3$: calc.: C, 77.12%; H, 5.75%. found: C, 76.96%; H, 5.82%.

1-(3-(Dimethylethyl)-2-hydroxy-5-methoxyphenyl)-2-naphthol

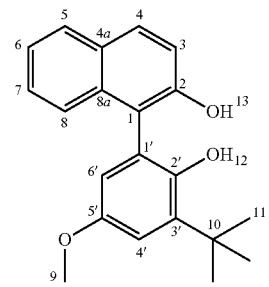 [SMILES: COc1cc(-c2c(O)ccc3ccccc23)c(O)c(C(C)(C)C)c1]

The electrolysis is conducted according to AAV1 in an undivided flange cell with a BDD anode. For this purpose, 0.72 g (5 mmol, 1.0 equiv.) of 2-naphthol and 2.77 g (15 mmol, 3.0 equiv.) of 2-(dimethylethyl)-4-methoxyphenol are dissolved in 27 ml of HFIP and 6 ml of MeOH, 0.68 g of methyltriethylammonium methylsulphate (MTES) is added and the electrolyte is transferred to the electrolysis cell. The solvent and unconverted amounts of reactant are removed under reduced pressure after the electrolysis, the crude product is purified on silica gel 60 in the form of a "flash chromatography" in 9:1 eluent (CH:EA) and the product is obtained as a colourless solid.

Yield: 1.05 g (63%, 3.2 mmol)
GC (hard method, HP-5): $t_R$=15.75 min
$R_f$(CH:EA=4:1)=0.43
$m_p$=139.9° C. (recrystallized from DCM/CH)
$^1$H NMR (400 MHz, CDCl$_3$) δ=1.46 (s, 9H, 11-H), 3.77 (s, 3H, 9-H), 4.72 (s, 1H, 2'-H), 5.36 (s, 1H, 2-H), 6.63 (d, 1H, 6'-H), 7.08 (d, 1H, 4'-H), 7.32 (d 1H, 3-H), 7.50-7.35 (m, 3H, 6-H/7-H/8- H), 7.87-7.83 (m, 1H, 5-H), 7.89 (d, 1H, 4-H);

Couplings: $^3J_{3\text{-}H,\ 4\text{-}H}$=8.9 Hz; $^4J_{4\text{-}H,\ 6'\text{-}H}$=3.1 Hz;
$^{13}$C NMR (101 MHz, CDCl$_3$) δ=29.41 (C-11), 35.19 (C-10), 55.68 (C-9), 111.95 (C-6'), 114.18 (C-1), 115.87 (C-4'), 117.63 (C-3), 119.16 (C-1'), 123.89, 124.15 (C-6/C-8), 127.38 (C-7), 128.31 (C-5), 129.19 (C-4a), 130.97 (C-4), 132.99 (C-8a), 139.05 (C-3'), 146.93 (C-2'), 151.94 (C-2), 153.41 (C-5').

HRMS for C$_{21}$H$_{22}$O$_3$(ESI+) [M+Na$^+$]: calc.: 345.1467. found: 345.1465.
MS (EI, GCMS): m/z (%): 322 (100) [M]$^+$, 307 (38) [M-CH$_3$]$^+$.
Elemental analysis for C$_{21}$H$_{22}$O$_3$: calc.: 78.23%; H, 6.88%. found: C, 78.18%; H, 6.82%.

Synthesis of the Chlorophosphites

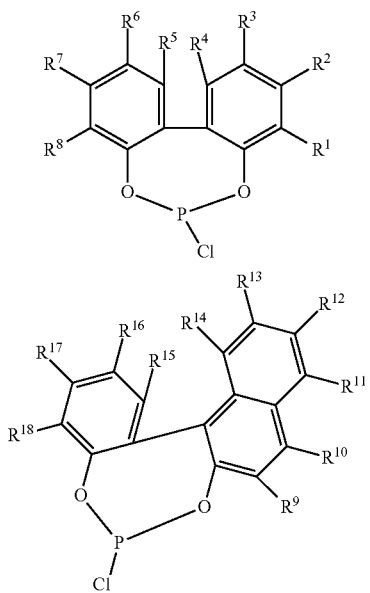

For the preparation of the inventive compounds, various chlorophosphites are required, specifically those having a biphenol unit on the one hand and those having a naphthyl-phenyl unit on the other hand. In the case of the compounds having the general structure (IV), three naphthyl phenyl units are required.

Given here as an illustrative example is 6-chlorodibenzo[d,f][1,3,2]dioxaphosphepine, which can be prepared according to DE 10 2008 043 584. All other chlorophosphites can be prepared in an analogous manner, i.e. by addition of phosphorous trichloride in the presence of a base. In this regard, see also "Phosphorus(III) Ligands in Homogeneous Catalysis—Design and Synthesis" by Paul C. J. Kamer and Piet W. N. M. van Leeuwen; John Wiley and Sons, 2012; inter alia p. 94 ff. and the references cited therein.

Since chlorophosphites formed from binol (1,1'-binaphthol) are prepared in an analogous manner to those having a biphenol unit, those chlorophosphites having a naphthyl-phenyl unit are also synthesized in an analogous manner.

Synthesis of the Inventive Compounds

The inventive compounds can be prepared by various routes. Three possible routes are shown in the schemes below.

The reaction routes shown are shown merely for illustrative purposes and in a simplified form. Thus, if required, base or solvent may be used in addition in all steps. These are sufficiently well known to those skilled in the art and can be found in the technical literature, such as "Phosphorus(III) Ligands in Homogeneous Catalysis—Design and Synthesis" by Paul C. J. Kamer and Piet W. N. M. van Leeuwen; John Wiley and Sons, 2012; inter alia p. 94 ff. and the references cited therein.

Reaction scheme for a compound of formula (I)

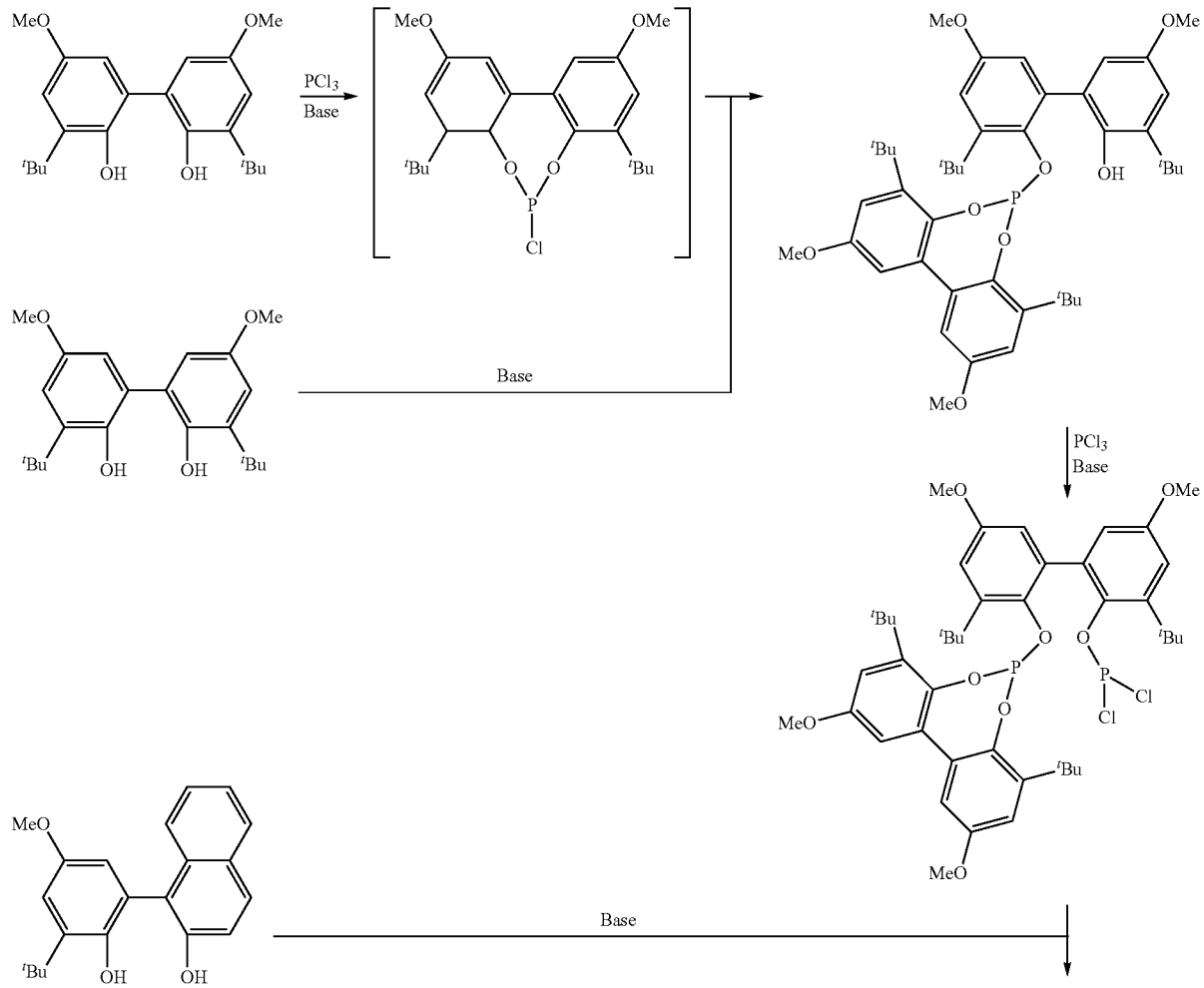

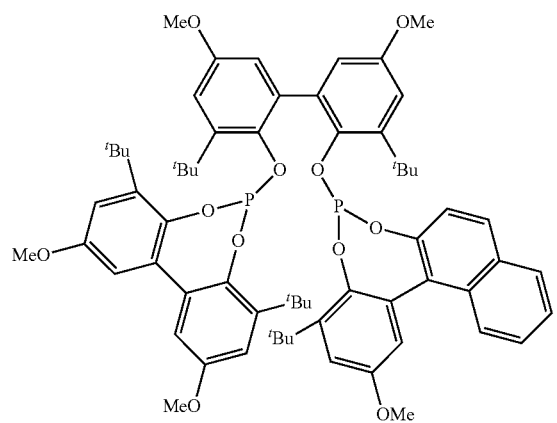
Reaction scheme for a compound of formula (II)
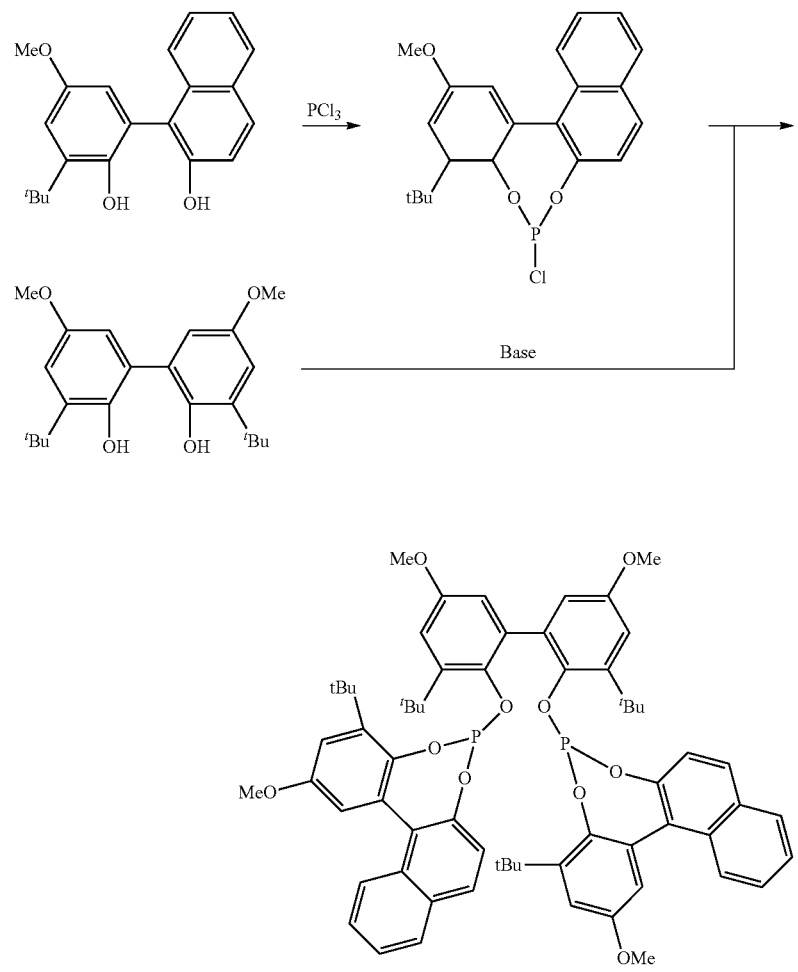

Reaction scheme for a compound of formula (III)
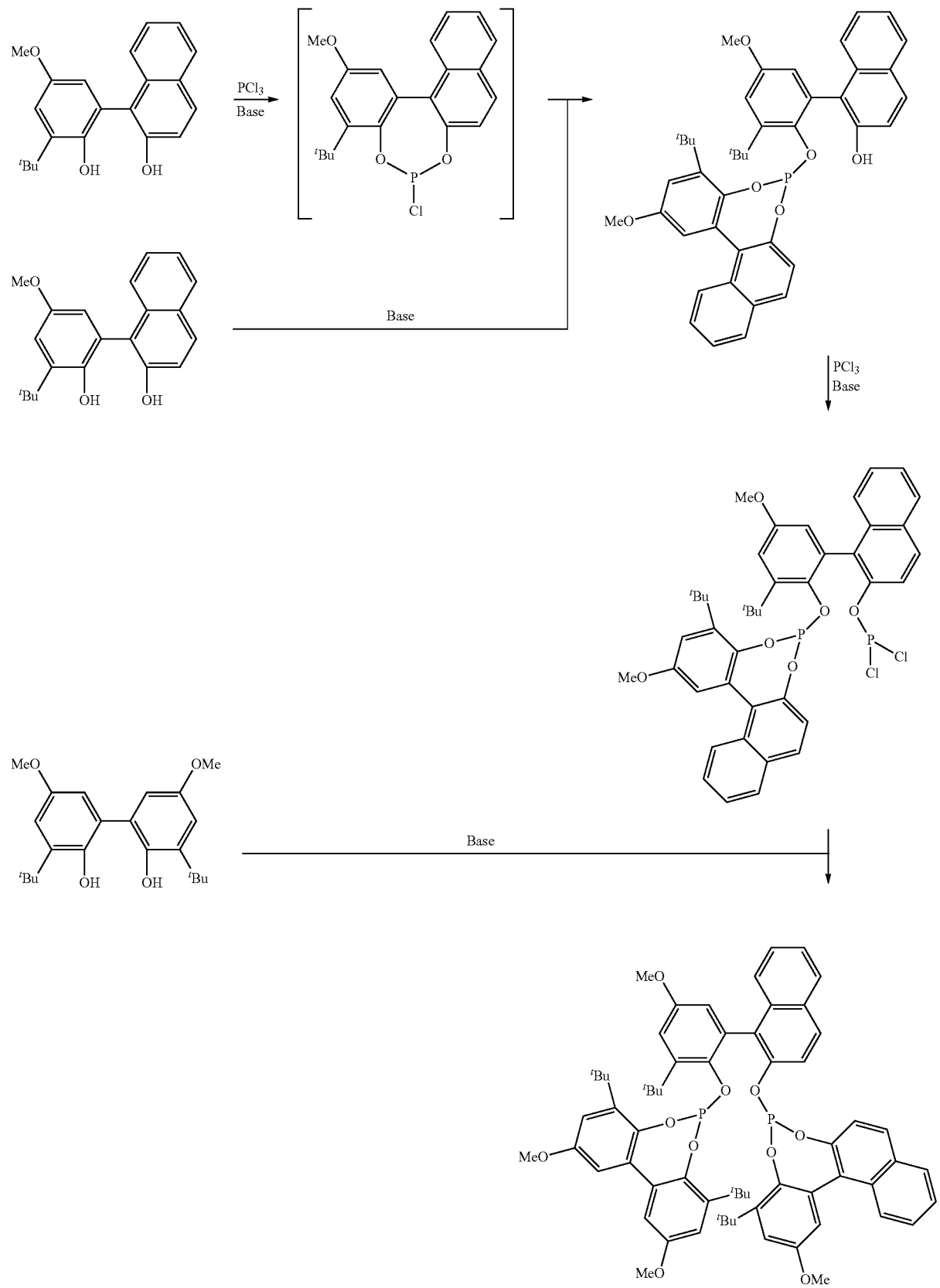

Reaction scheme for a compound of formula (IV)

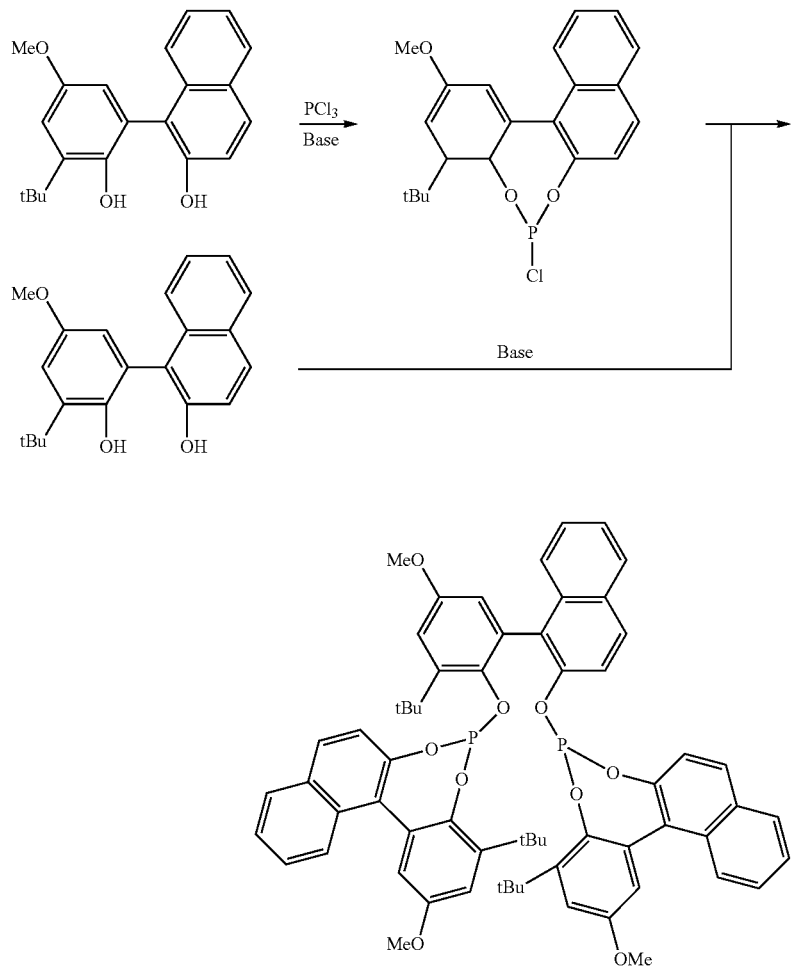

For the first time, a synthesis route by which the inventive compounds can be prepared by an efficient route has been illustrated. The bisphosphites obtained in this way fulfil the objective, since these, for the first time, have a naphthyl-phenyl unit as outer unit.

The invention claimed is:

1. Compound having one of the four general structures I to IV:

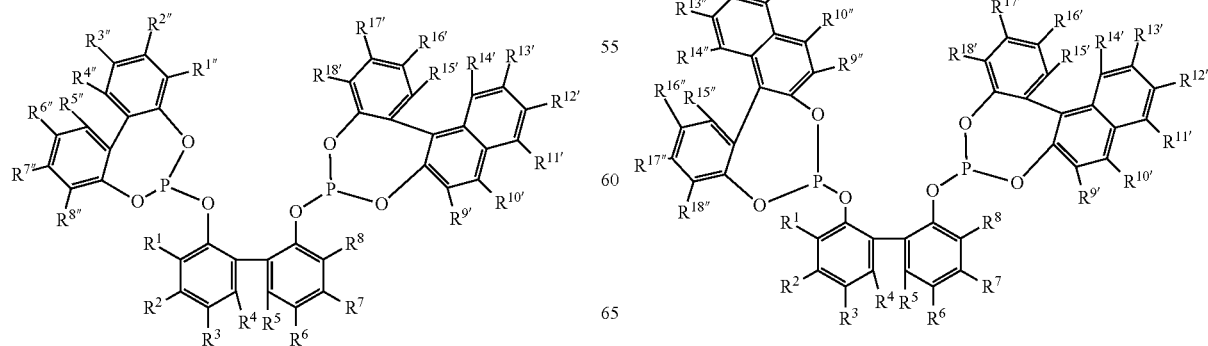

-continued

-continued (III)

(IV)

where
$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$ are selected from:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —S-alkyl, —S-aryl, halogen, COO—$(C_1$-$C_{12})$-alkyl, CONH—$(C_1$-$C_{12})$-alkyl, —CO—$(C_1$-$C_{12})$-alkyl, —CO—$(C_6$-$C_{20})$-aryl, —COOH, —OH, —SO$_3$H, —CN, —NH$_2$, —N[$(C_1$-$C_{12})$-alkyl]$_2$;
$R^{1\prime}, R^{2\prime}, R^{3\prime}, R^{4\prime}, R^{5\prime}, R^{6\prime}, R^{7\prime}, R^{8\prime}, R^{9\prime}, R^{10\prime}, R^{11\prime}, R^{12\prime}, R^{13\prime}, R^{14\prime}, R^{15\prime}, R^{16\prime}, R^{17\prime}, R^{18\prime}$ are selected from:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —S-alkyl, —S-aryl, halogen, COO—$(C_1$-$C_{12})$-alkyl, CONH—$(C_1$-$C_{12})$-alkyl, —CO—$(C_1$-$C_{12})$-alkyl, —CO—$(C_6$-$C_{20})$-aryl, —COOH, —OH, —SO$_3$H, —NH$_2$, —N[$(C_1$-$C_{12})$-alkyl]$_2$;
$R^{1\prime\prime}, R^{2\prime\prime}, R^{3\prime\prime}, R^{4\prime\prime}, R^{5\prime\prime}, R^{6\prime\prime}, R^{7\prime\prime}, R^{8\prime\prime}, R^{9\prime\prime}, R^{10\prime\prime}, R^{11\prime\prime}, R^{12\prime\prime}, R^{13\prime\prime}, R^{14\prime\prime}, R^{15\prime\prime}, R^{16\prime\prime}, R^{17\prime\prime}, R^{18\prime\prime}$ are selected from:
—H, —$(C_1$-$C_{12})$-alkyl, —O—$(C_1$-$C_{12})$-alkyl, —O—$(C_6$-$C_{20})$-aryl, —$(C_6$-$C_{20})$-aryl, —S-alkyl, —S-aryl, halogen, COO—$(C_1$-$C_{12})$-alkyl, CONH—$(C_1$-$C_{12})$-alkyl, —CO—$(C_1$-$C_{12})$-alkyl, —CO—$(C_6$-$C_{20})$-aryl, —OH, —SO$_3$H, —NH$_2$, —N[$(C_1$-$C_{12})$-alkyl]$_2$;
where the alkyl and aryl groups mentioned may be substituted.

2. Compound according to claim 1,
where $R^1, R^2, R^3, R^4, R^5, R^6, R^7, R^8$ are selected from:
—H, —$(C_1$-$C_{12})$-alkyl, —O—$(C_1$-$C_{12})$-alkyl, —O—$(C_6$-$C_{20})$-aryl, —S-alkyl, —S-aryl.

3. Compound according to claim 1,
where $R^{1\prime}, R^{2\prime}, R^{3\prime}, R^{4\prime}, R^{5\prime}, R^{6\prime}, R^{7\prime}, R^{8\prime}$ are selected from:
—H, —$(C_1$-$C_{12})$-alkyl, —O—$(C_1$-$C_{12})$-alkyl, —O—$(C_6$-$C_{20})$-aryl, —S-alkyl, —S-aryl.

4. Compound according to claim 1,
where $R^{1\prime\prime}, R^{2\prime\prime}, R^{3\prime\prime}, R^{4\prime\prime}, R^{5\prime\prime}, R^{6\prime\prime}, R^{7\prime\prime}, R^{8\prime\prime}$ are selected from:
—H, —$(C_1$-$C_{12})$-alkyl, —O—$(C_1$-$C_{12})$-alkyl, —O—$(C_6$-$C_{20})$-aryl, —S-alkyl, —S-aryl.

5. Compound according to claim 1,
where $R^{9}, R^{10}, R^{11}, R^{12}, R^{13}, R^{14}, R^{15}, R^{16}, R^{17}, R^{18}$ are selected from:
—H, —$(C_1$-$C_{12})$-alkyl, —O—$(C_1$-$C_{12})$-alkyl, —O—$(C_6$-$C_{20})$-aryl, —S-alkyl, —S-aryl.

6. Compound according to claim 1,
where $R^{9\prime}, R^{10\prime}, R^{11\prime}, R^{12\prime}, R^{13\prime}, R^{14\prime}, R^{15\prime}, R^{16\prime}, R^{17\prime}, R^{18\prime}$ are selected from:
—H, —$(C_1$-$C_{12})$-alkyl, —O—$(C_1$-$C_{12})$-alkyl, —O—$(C_6$-$C_{20})$-aryl, —S-alkyl, —S-aryl.

7. Compound according to claim 1,
where $R^{9\prime\prime}, R^{10\prime\prime}, R^{11\prime\prime}, R^{12\prime\prime}, R^{13\prime\prime}, R^{14\prime\prime}, R^{15\prime\prime}, R^{16\prime\prime}, R^{17\prime\prime}, R^{18\prime\prime}$ are selected from:
—H, —$(C_1$-$C_{12})$-alkyl, —O—$(C_1$-$C_{12})$-alkyl, —O—$(C_6$-$C_{20})$-aryl, —S-alkyl, —S-aryl.

8. Compound according to claim 1,
where the compound has the general structure (I).

9. Compound according to claim 1,
where the compound has the general structure (II).

10. Compound according to claim 1,
where the compound has the general structure (III).

11. Compound according to claim 1,
where the compound has the general structure (IV).

* * * * *